(12) United States Patent
Prokop et al.

(10) Patent No.: US 6,383,478 B1
(45) Date of Patent: May 7, 2002

(54) POLYMERIC ENCAPSULATION SYSTEM PROMOTING ANGIOGENESIS

(75) Inventors: Ales Prokop; Mikhail M. Dikov, both of Nashville; Phillip Williams, Lebanon; Jeffrey M. Davidson, Nashville, all of TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 09/556,743

(22) Filed: Apr. 21, 2000

Related U.S. Application Data

(60) Provisional application No. 60/130,615, filed on Apr. 22, 1999, now abandoned.

(51) Int. Cl.⁷ .............................................. A61K 31/74
(52) U.S. Cl. .................................................. 424/78.08
(58) Field of Search ....................... 424/78.08

(56) References Cited

U.S. PATENT DOCUMENTS 3,560,424 A * 2/1971 Glaser et al. ............. 260/29.6
3,799,902 A * 3/1974 Anderson et al. ......... 260/29.6

FOREIGN PATENT DOCUMENTS

| DE | 136702 | * 7/1979 |
| DE | 152287 | * 11/1981 |
| DE | 19604173 | * 8/1997 |

* cited by examiner

Primary Examiner—Alton N. Pryor
(74) Attorney, Agent, or Firm—Benjamin Aaron Adler

(57) ABSTRACT

The present invention provides a convenient polymeric film or microparticulate vehicle to deliver protein factors into appropriate body sites to induce appropriate therapeutic effects. It also improves the existing methodologies for immunoisolation of non-human pancreatic islets (via microencapsulation) to protects them from the immunologically-different host. This invention demonstrates how vascularization and angiogenesis can be induced by means of addition of proper angiogenic factors. The angiogenesis is sustained over a long period of time, depending on the release characteristics of the polymeric matrix. Three-dimensional polymeric structures (mesh or perforated tubing and film) are used as resident materials for microcapsules bearing islets. Blood capillaries are generated outside the capsules and penetrate through the implant openings to ingrow into the vicinity of capsules/islets.

34 Claims, No Drawings

POLYMERIC ENCAPSULATION SYSTEM PROMOTING ANGIOGENESIS

CROSS-REFERENCE TO RELATED APPLICATION

This non-provisional patent application claims benefit of provisional patent application U.S. Serial No. 60/130,615, filed Apr. 22, 1999, now abandoned.

FEDERAL FUNDING LEGEND

This invention was produced in part using funds obtained through a grant from the national Institutes of Health. Consequently, the federal government has certain rights in this invention.

BACKGROUND OF THE INVENTION

1. Field of the Invention

The present invention relates generally to the fields of pharmaceutical sciences, protein chemistry, polymer chemistry, colloid chemistry, immunology, and biomedical engineering. More specifically, the present invention relates to a novel delivery system for vascularization agents and other growth factors and drugs.

2. Description of the Related Art

Microparticulate systems are particles having diameter 1–2,000 $\mu$m (2 mm), more preferably 100–500 $\mu$m (microcapsules). Nanoparticles range from 1–1000 nm (1 $\mu$m=1,000 nm), preferably 10–300 nm. Alternatively, polymeric films of 0.5 to 5-mm thickness can be made. Also, absorbable or nonabsorbable polymers can be coated with a polymeric film. Collectively, these systems will be denoted as drug delivery vehicles. All these vehicles can be formed from variety of materials, including synthetic polymers and biopolymers (proteins and polysaccharides) and can be used as carriers for drugs and other biotechnology products, such as growth factors and genes.

In the scientific realm of controlled drug delivery, the drug delivery vehicles are formed in a mixture with the agent to be encapsulated for subsequent sustained release. A number of different techniques are used to make these vehicles from synthetic or natural polymers. These techniques include phase separation, precipitation, solvent evaporation, emulsification, spray drying, casting of polymers into a polymeric sheet, or any combination thereof [Desay, P. B. Microencapsulation of drugs by pan and air suspension technique. Crit. Rev. Therapeut. Drug Carrier Syst., 5: 99–139 (1988); Berthold, A., Cremer, K., Kreuter, J. Preparation and characterization of chitosan microspheres as drug carrier for prednisolone sodium phosphate as model antiinflammatory drugs. J. Controlled Release 39: 17–25 (1996); Watts, P. J., Davies, H. C., Melia, C. D. Microencapsulation using emulsification/solvent evaporation: An overview of techniques and applications. Crit. Rev. Therapeut. Drug Carrier Syst. 7: 235–159 (1990); Cowsar, D. R., Tice, T. R., Gilley, R. M., English, J. P. Poly(lactide-co-glycolide) microcapsules for controlled release of steroids. Methods Enzymol. 112: 101–116 (1985); Genta, I., Pavanetto, F., Conti, B., Ginnoledi, P., Conte, U. Spray-drying for the preparation of chitosan microspheres. Proc. Int. Symp. Controlled Release Mater. 21: 616–617 (1994)].

Polymeric vehicles can be prepared either from preformed polymers, such as polylactic acid, polylactic-glycolic acid [Cohen, S., Yoshioka, T., Lucarolli, M., Hwang, L. H., Langer, R. Controlled delivery systems for proteins based on poly(lactic/glycolic acid) microspheres. Pharm. Res. 8: 713–720 (1991)], or from a monomer during polymerization, such as polyalkylcyanoacrylates [Al-Khouri-Fallouh, N., Roblet-Trempel, L., Fessi, M, Devissaguet, J.-P., Puisieux, F. Development of new process for the manufacture of polyisobutylcyanoacrylate nanoparticles. Int. J. Pharm. 28: 125–132 (1986)]. Both of these technologies have limited application due to the use of organic solvents, which leave residual organic solvents in the final product. Although the polyalkylcyanoacrylate nanoparticulate technology is also available in a water-based system [Couvreur, P., Roland, M., Speiser, P. Biodegradable submicroscopic particles containing a biologically active substance and compositions containing them. U.S. Pat. No. 4,329,332 (1982)], animal studies demonstrated the presence of toxic degradation products [Cruz, T., Gaspar, R., Donato, A., Lopes, C. Interaction between polyalkylcyanoacrylate nanoparticles and peritoneal macrophages: MTT metabolism, NBT reduction, and NO production. Pharm. Res. 14: 73–79 (1997)].

Cell encapsulation [Chang, T. M. Hybrid artificial cells: Microencapsulation of living cells. ASAIO Journal 38: 128–130 (1992)] is a related technology that has also been explored for the purpose of making micro- and nanoparticles. Such particles can be formed either by polymer precipitation, following the addition of a non-solvent or by gelling, following the addition of a small inorganic ion (salt) and a complexing polymer (of an opposite charge). If a long enough time is allowed the particle interior (core) can be completely gelled. Usually, the inner core material is of a polyanionic nature (negatively charged polymer). The particle membrane (shell) is made from a combination of polycation (positively charged polymer) and polyanion. The core material is usually atomized (nebulized) into small droplets and collected in a receiving bath containing a polycationic polymer solution. The reciprocal structure is also possible. In this scenario, core material is polycationic and the receiving bath is polyanionic. Several binary polymeric encapsulation systems (resulting from two polymers) have been described [Prokop, A., Hunkeler, D., DiMari, S., Haralson, M. A., Wang, T. G. Water soluble polymers for immunoisolation. I. Complex caocervation and cytotoxicity. Advances in Polymer Science, 136: 1–51 (1998)]. These systems are inadequate due to the fact that the membrane parameters are governed by a single chemical complex resulting from the ionic interactions. The inability to adjust independently particle parameters hinders the success of these systems.

In an effort to overcome these severe limitations, new multicomponent polymeric micro- and nanoparticles were designed that permit independent modification of mechanical strength and permeability [Prokop, A., Hunkeler, D., Powers, A. C., Whitesell, R. R., Wang, T. G. Water soluble polymers for immunoisolation. II. Evaluation of multicomponent microencapsulation systems. Advances in Polymer Science, 136: 52–73 (1998)]. Over one thousand combinations of polyanions and polycations were examined as polymer candidates suitable for encapsulation of living cells. Thirty-three combinations were found to be usable. However, microcapsules are not always best suited as delivery vehicles because of their relatively large size. In addition, the composition and concentrations claimed in [Wang, T. G., Lacik, I., Brissova, M., Anilkumar, A. V., Prokop, A., Powers, A. C. Encapsulation system for the immunoisolation of living cells. U.S. Pat. No. 599,790, 1997] do not allow for the generation of small nanoparticles, suitable for injectable drug delivery. Such system has recently been described in a patent application [Prokop, A.:

Micro- and nano-particulate polymeric delivery system, U.S. patent application, 1997].

Diabetes is a chronic disease, characterized by a high morbidity and mortality rate due to major complications (blindness, renal failure, and neuropathy) [The Diabetes Control and Complications Trial Research Group (DCCT). The effect of intensive treatment of diabetes on the development and progression of long-term complications in insulin dependent diabetes mellitus, New England J. Med. 329: 977–986 (1993)]. During the past 10 years it has become clear that none of the alternative treatment strategies (such as gene therapy, islet transplantation, beta cell bioartificial pancreas) provide a sufficient benefit to risk ratio. It is, nevertheless, difficult using current technologies to maintain normal blood sugar levels in individuals with diabetes. Considerable research has been devoted to the development of alternative methods for reestablishing normoglycemia. Pancreas and islet transplantation results have been disappointing, and the procedures are unlikely to receive widespread use [Lacy, P. E. Islet transplantation—The future, in: *Pancreatic Islet Cell Transplantation*, Ricordi, C., ed., R. G. Landes, Austin, pp. 394–399, 1992; Mintz, D. H. and Alejandro, R. Islet cell transplantation, In: *Pancreatic Islet Cell Transplantation*, Ricordi C, ed., R. G. Landes, Austin, pp. 1–6, 1992]. The use of non-human islets is limited by their immediate rejection and destruction by the recipient unless a potent immune suppressive therapy is applied. An ideal treatment for diabetes would isolate the donor animal islets from the host immune system while allowing other islet functions such as metabolism and insulin production to proceed without restriction.

Encapsulation of living islets from animals may overcome the problems facing the whole-organ transplantation. Encapsulating the living islets in a protective membrane or microcapsules would allow insulin to be secreted, yet prevent the immune system from rejecting the islet [Lim, F. and Sun, A. M. Microencapsulated islets as bioartificial endocrine pancreas, Science 210: 908–910 (1989)]. The recipient would not need to be placed on anti-rejection drug regimen as currently practiced in whole-organ transplantation. Since these drugs themselves pose significant danger to the patient, the advantages of transplanting encapsulated islets are evident.

A number of encapsulation processes are available today, however, none of these methods fulfill the requirements for transplantation [Calafiore, R. The large-scale microencapsulation of isolated and purified human islets of Langerhans, In: *Pancreatic Islet Cell Transplantation*, Ricordi C, ed., R. G. Landes, Austin, pp. 207–214, 1992; Lanza, R. P., Sullivan, S. J., Monaco, A. P. and Chick, W. L. The hybrid artificial pancreas: Diffusion and vascular devices, In: *Pancreatic Islet Cell Transplantation*, Ricordi C, ed., R. G. Landes, Austin, pp. 223–237, 1992; Soon-Shiong, P., Heitz, R. E., Merideth, N., Yao, Q. X., Yao, Z., Zheng, T., Murphy, M., Maloney, M. K., Schmehl, M., Harris, M., Mendez, R., Mendez, R. and Sandford, P. A. Insulin independence in a type I diabetic patient after encapsulated islet transplantation, Lancet 343: 950–951 (1994); Weber, C. J. et al. Xenografts of microencapsulated rat, canine, porcine and human islets, In: *Pancreatic Islet Cell Transplantation*, Ricordi C, ed., R. G. Landes, Austin, pp. 177–190 1992]. Methods such as interfacial polymerization or chemical crosslinking of polymers use organic solvents or toxic chemicals (which are also toxic to the encapsulated living cells). The technique developed by Lim and Sun, employing an alginate/polylysine membrane system, has been implemented with some success [Lim, F. and Sun, A. M. Microencapsulated islets as bioartificial endocrine pancreas, Science 210: 908–910 (1989)]. However, transplantation with this type of capsule has been limited by fibrosis of the capsules in large animals (resulting in anoxia and death of islets), and a limited life span of the capsules. Clearly, further progress in the design of capsules for immunoisolation of islets and in the facilitation of their survival is needed.

Adverse effects of anoxia can be partially alleviated by the ability of islets to upregulate synthesis of angiogenic factors under hypoxia. It has been shown that the expression of VEGF in isolated islets is upregulated following a period of hypoxia and hypoglycemia in vitro [Gorden, D. L., Mandriota, S. J., Montesano, R., Orci, L., Pepper, M. S. Vascular endothelial growth factor is increased in devascularized rat islets of Langerhans in vitro, Transplantation 63: 436–443 (1997)] and may partially relieve a lack of oxygen in the initial phases of transplant fibrosis. However it cannot achieve a complete abrogation. In addition, this capability may be impaired due to islet damage during the enzymatic digestion process that isolates the islets from the pancreas.

Recent advances in the understanding the molecular mechanisms of wound healing process and of normal and pathological angiogenesis provide solid basis for the clinical application of vascularizing growth factors. Further clinical development is only possible through designing regimens that can practically address the problems of bioavailability.

The prior art is deficient in the lack of polymer encapsulation systems which promote vascularization of tissues surrounding transplanted capsules and which prevent fibrosis from isolating the capsule contents. The present invention fulfills this longstanding need and desire in the art.

SUMMARY OF THE INVENTION

The present invention is based on a unique formulation method using multicomponent water-soluble polymers formed into polymeric sheets. This preparation permits modification to a desirable size, provides adequate mechanical strength and exhibits exceptional permeability and surface characteristics.

One embodiment of present invention is a polyanionic/polycationic polymeric composition further comprising a protein which may be an angiogenic stimulating factor, a growth factor, or an extracellular matrix protein. Possible polyanion core components are kappa carrageenan, low-esterified pectin (polygalacturonic acid), polyglutamic acid; CMC, carboxymethylcellulose; ChS-6, chondroitin sulfate-6; ChS-4, chondroitin sulfate-4; F-68, Pluronic, CMC, ChS-6, ChS-4, and collagen. Representative cationic shell components include polyvinylamine, spermine hydrochloride, protamine sulfate, polyethyleneimine, polyethyleneimine-ethoxylated, polyethyleneimine, epichlorhydrin modified, quartenized polyamide and polydiallyldimethyl ammonium chloride-co-acrylamide, and low molecular-weight chitosan. In a preferred embodiment, the polymeric film is synthesized from the polyanions high viscosity sodium alginate and cellulose sulfate and the calcium chloride and poly (methylene-co-guanidine) hydrochloride (PMCG) (polycation). Possible angiogenic stimulating factors include vascular endothelial growth factor (VEGF), angiopoietin (APO), transforming growth factor (TGF) TGFβ, acidic fibroblast growth factor (FGF) aFGF, basic fibroblast growth factor bFGF, and the combination of aFGF and bFGF collectively referred to as FGF. Platelet derived growth factor (PDGF) is a possible growth factor, while possible extracellular matrix components include heparin, heparan sulfate, hyaluronic acid, fibronectin, laminin, and perlecan.

It is contemplated that a pharmaceutical composition may be prepared using a drug encapsulated in the said vehicle of the present invention. In such a case, the pharmaceutical composition may comprise a drug (vascularization agent) and a biologically acceptable matrix. A person having ordinary skill in this art readily would be able to determine, without undue experimentation, the appropriate concentrations of said biotechnology products, matrix composition and routes of administration of the vehicle of the present invention.

Another embodiment of the present invention is the encapsulation of animal cells in a polymer containing an angiogenic stimulating factor. The vascularization factor promotes vascularization around the microencapsulated cells to prevent hypoxia of the cells within the microcapsules. In addition, it prevents the formation of fibrous tissue around the microcapsules, resulting in the isolation of the microcapsules. The polymer may also include growth factors in addition to the angiogenic stimulating factor.

In yet another embodiment of the present invention, the area in which the cell are to be implanted may be prevascularized by placing a polymer mesh or capsule containing an angiogenic stimulating factor in the individual for at least 2 weeks prior to implanting encapsulated cells.

Preferably, the animal cells are pancreatic islet cells. The pancreatic islet cells may be implanted as microencapsulated cells. Growth factor may also be incorporated in the polymer encapsulating the cells or may be present in polymeric films, microcapsules, or nanoparticles encapsulated along with the islet cells. For example, microencapsulated pancreatic islet cells and nanoparticulate FGF may be implanted together in a capsule in the peritoneum of the kidney. To slow the release of the growth factor, polydextran aldehyde may be used to crosslink the growth factor to the polymer.

In another embodiment of the present invention, a method is provided for accelerating in vivo wound healing by placing a polymeric composition containing growth factor in proximity to a wound. Platelet derived growth factor would be especially efficacious in promoting wound healing. Alternatively, the form of the polymer may be a polymeric film containing FGF, nanoparticle-FGF, or FGF-hydrogel-coated (and possibly crosslinked with polydextran aldehyde) bioresorbable film for wound healing. In additional, The FGF can be crosslinked to the polymer via via Schiff-base polydextran aldehyde complex to slow release of the growth factor.

In another embodiment of the current invention, a dialysis based method of making polymeric sheets for drug and cell encapsulation is described, including the following steps: (1) introduction of a solution of polyanionic monomers into a sterile dialysis cassette; (2) immersion of said cassette in a stirred reactor containing a polycationic shell solution, (3) diffusion of the polycationic solution inside the cassette to form a polymeric film. The reaction may proceed for few minutes to few hours. For many combinations of polymers, the initial formation of film is observed within few minutes. However considerable time is required to mature into mechanically self-sustainable films. The resulting polymeric film has an excess of positive charge on the outside of the film which may be neutralized by incubation with a dilute polyanionic solution. Proteins may be incorporated in the resulting polymer by adding the protein to the polyanion solution during dialysis. The said composition can be used for production of polymeric films, microcapsules and nanoparticles.

Yet another embodiment of the present invention is the coating of prefabricated structures with a polymer containing a desired protein in a coating process involving sequential application of polyanion and polycation coats. The protein in question is included in the polyanion coat.

A further embodiment is a three-dimensional matrix which provides a resident structure for microencapsulated pancreatic islet cells. Careful selection of the polymers forming the three-dimensional structure permits the slow release of an embedded vascularization agent. In this manner, ingrowth of blood capillaries towards the encapsulated pancreatic islets is encouraged. Both polymers and agent encourage capillary network development and inhibit or eliminate growth of the dense and impermeable fibrotic cellular structures that are often associated with implant failure.

Other and further aspects, features, and advantages of the present invention will be apparent from the following description of the presently preferred embodiments of the invention given for the purpose of disclosure.

DETAILED DESCRIPTION OF THE INVENTION

As appearing herein, the following terms shall have the definitions set out below.

As used herein, the term "drug" shall refer to a chemical entity of varying molecular size (both small and large) exhibiting a therapeutic effect in animals and humans.

As used herein, the term "reactor" refers to an enclosed vessel provided with or without stirrer, allowing a reaction to proceed in liquid or gas phases.

As used herein, the term "film vehicle" shall refer to a microscopic gelled solid object of slab geometry.

As used herein, the term "microcapsule" shall refer to microscopic (few micrometers in size to few millimeters) solid object, essentially of regular spherical shape, exhibiting a liquid core and a semipermeable shell.

As used herein, the term "nanoparticle" shall refer to submicroscopic (less than 1 micrometer in size) solid object, essentially of regular or semi-regular shape.

"As used herein, the term "shell" refers to an insoluble polymeric electrostatic complex composed of internal core polymer(s) and external bath polymer(s) molecularly bonded (gelled) in close proximity.

As used herein, the term "structural (gelling) polymer" shall refer to polymers, which can form semi-solid gelled structures by means of small ion complexing.

As used herein, the term "core polymer" shall refer to an internal part of the microcapsule, nanoparticle or polymeric film.

In the description of the present invention, the following abbreviations may be used: SA-HV, high viscosity sodium alginate; CS, cellulose sulfate; k-carr, kappa carrageenan; LE-PE, low-esterified pectin (polygalacturonic acid); PGA, polyglutamic acid; CMC, carboxymethylcellulose; ChS-6, chondroitin sulfate-6; ChS-4, chondroitin sulfate-4; F-68, Pluronic copolymer; PVA, polyvinylamine; 3PP, pantasodium tripolyphosphate; PMCG, poly(methylene-co-guanidine) hydrochloride; SH, spermine hydrochloride; PS, protamine sulfate; PEI, polyethyleneimine; PEI-eth, polyethyleneimine-ethoxylated; PEI-EM, polyethyleneimine, epichlorhydrin modified; Q-PA, quartenized polyamide; pDADMAC-co-acrylamide, polydiallyldimethyl ammonium chloride-co-acrylamide; PBS, phosphate-buffered saline; ECM, extracellular matrix molecule; aFGF, acidic fibroblast growth factor; bFGF, basic fibroblast growth factor; VEGF, vascular endothelial growth factor; TGFβ, transforming growth factor β; APO, angiopoietin.

The present invention is directed to a composition of matter comprising various polyanionic/polycationic polymer compositions incorporating angiogenic stimulating factors, growth factors, or extracellular matrix proteins. Among useful polyanions for making polymeric films, capsules and nanoparticles are k-carr, LE-PE, PGA, CMC, ChS-6, ChS-4, and collagen. Possible polycations include PVA, SH, PS, PEI, PEI-eth, PEI-EM, Q-PA and pDADMAC-co-acrylamide, and low molecular-weight chitosan, among others.

The present invention can be used to stimulate vascularization around a polymeric capsule which may include a drug or microencapsulated cells. Among useful angiogenic stimulating growth factors for this purpose are VEGF, aFGF and bFGF collectively referred to as FGF, APO, and TGFβ.

An area may be prevascularized by placing a retrievable polymeric mesh or capsule incorporating an angiogenic stimulating factor in an individual for at least 2 weeks.

The instant invention is especially useful for the implantation of microencapsulated pancreatic islet cells. A growth factor may also be included in either the polymer encapsulating the cells or in a separate polymeric composition to stimulate the growth of the pancreatic islet cells. Release of the growth factor may be slowed by crosslinking the growth factor to the polymer with polydextran aldehyde. The encapsulated pancreatic islet cells and growth factor may be implanted in a capsule in the peritoneum of the kidney.

In addition, the present invention describes a method of accelerating in vivo wound healing by placing the polymeric vehicles containing an appropriate angiogenic growth factor in proximity to a wound. Representative growth factors include platelet derived growth factor and fibroblast growth factors. Release of the growth factors may be slowed by crosslinking the factors to the polymer with polydextran aldehyde. The present invention provides a dialysis process for making sterile polyanionic/polycationic polymeric compositions. A particularly usable combination is anionically charged alginate/CS, cationically charged PMCG/calcium chloride. Proteins such as angiogenic growth factors may be incorporated into these compositions by including them in the polyanion mixture during dialysis. Even if a protein is cationically charged (as is the case of bFGF), it is still incorporated into the multicomponent polyanionic mixture, as the formed electrostatic complex between the anions and such growth factor is water soluble at the concentrations of angiogenic growth factor used.

Additionally, the method of coating of prefabricated polymeric films and other three-dimensional structures with the polyanion/polycation polymeric composition is described. This is done by a sequential coating process where polyanion and polycation coats are alternatively applied. The material can be coated with protein factors by including these factors in the polyanion coat.

Effective treatment of medical conditions in the human body often requires the creation or restoration of blood vessels. This vascularization, process can be the crucial step in therapies for highly dissimilar ailments, and its failure can mean the difference between long-term success and a brief improvement followed by decline or even death. Furthermore, the value of a newly-formed capillary subsystem can be undermined if a fibrous tissue formation occurs. These issues are addressed herein for the case of diabetes.

A three-dimensional matrix is suggested in this invention which provides a resident structure for microencapsulated pancreatic islet cells. Careful selection of the polymers forming the three-dimensional structure permits the slow release of an embedded vascularization agent. In this manner, ingrowth of blood capillaries towards the encapsulated pancreatic islets is encouraged. Both polymers and agent encourage capillary network development and inhibit or eliminate growth of the thick fibrotic cellular structures that are often associated with implant failure.

The following examples are given for the purpose of illustrating various embodiments of the invention and are not meant to limit the present invention in any fashion.

EXAMPLE 1

Polymeric Film Vehicle Production Process

A mold method, using the 1.5 ml Pierce (Rockford, Ill.) dialysis cassettes (with 10 k molecular weight cut-off) was been developed. A water solution of core polymers was prepared by weighing 0.6 g of CS and 0.6 g of high viscosity sodium alginate (Algin) and dissolving them for one hour in 100 cc of PBS by means of a magnetic bar and stirrer plate. A cationic shell solution consisting of 1 g of calcium chloride and 1 g of poly(methylene-co-guanidine) hydrochloride in 100 cc of water was also prepared. The polymers used were: high viscosity sodium alginate (SA-HV) from Kelco/Merck (San Diego, Calif.) of molecular weight $4.6 \times 10^5$; cellulose sulfate, sodium salt (CS) from Janssen Chimica (Geel, Belgium) having an average molecular weight $1.2 \times 10^6$; and poly(methylene-co-guanidine) hydrochloride from Scientific Polymer Products, Inc. (Ontario, N.Y.), with average molecular weight $5 \times 10^3$. 1.5 ml of the core solution was incorporated via an injection port on the cassette. The cassette was then dipped in 150 ml of cationic solution and allowed to react for three hours.

Oligomers of cation and small inorganic cations penetrated through the dialysis membrane of the cassette and reacted with the internal core solution. The membrane was formed under aseptic conditions using sterile cassettes. The core solution is filter-sterilized (0.2 μm) prior to the application. After processing, the gelled film was aseptically cut off the cassette. The resulting semitransparent film was stable for many weeks in PBS solution. Since such films possess a positive charge, they were coated with diluted anionic polymers to introduce a negative charge. Two suitable anionic polymers are alginate (0.1% w/w) or carboxymethylcellulose (0.1% w/w), both exhibiting nonadhesive (tissue) properties. The coating was carried out by means of dipping the polymeric film into the above solution for 5 minutes, followed by a quick wash in PBS solution. Alternatively, polymeric films were coated with ⅕ concentration of the anionic Algin/CS solution as mentioned above. The films were stored in a moist state in a covered sterile Petri dish. In a separate experiment, polymeric films of a similar composition were prepared using 5 and 15 ml (maximum capacity) cassettes.

EXAMPLE 2

Angiogenic Factor-loaded Film Production Process

Using procedures similar to those in Example 1, the core solution contained an additional ingredient: 0.1–15 μg/ml bFGF (Upstate Biotechnology, Lake Placid, N.Y.). The gelled film contained almost all quantity of the factor supplied. The leakage of this factor to the external cationic bath was essentially zero due to the fact that this angiogenesis stimulating factor is about 15,000 daltons in size, larger than the molecular cut-off of the dialysis membrane. This was confirmed in another experiment using $^{125}$I-labeled factor. This film product presents a distinct advantage compared to the small encapsulation efficiency observed with standard microencapsulation technology.

EXAMPLE 3

Angiogenic Factor-loaded Microcapsule Production Process

Microcapsules were prepared using a standard microencapsulation technology described by us [Wang, et al., Encapsulation system for the immunoisolation of living cells. U.S. Pat. No. 5,997,900]. Again, as in Example 2, bFGF was dissolved in the core polymeric mixture, in quantities ranging from 0.1–15 µg/ml. The encapsulation efficiency was only 10–25% depending on the quantity supplied. Similarly, islets and bFGF were co-encapsulated in the same matrix.

EXAMPLE 4

Angiogenic Factor-loaded Nanoparticle Production Process

Nanoparticles loaded with 0.1–15 µg/ml (per capsule volume) bFGF were prepared. This particle was generated using a droplet-forming polyanionic solution composed of 0.1 wt-% high viscosity sodium alginate, 0.1 wt-% cellulose sulfate, and 0.1–15 µg/ml of FGF in water and corona-forming polycationic solution composed of 0.1 wt-% poly (methylene-co-guanidine)hydrochloride, 0.2 wt-% calcium chloride, and 1.0 wt-% Pluronic F-68 (BASF, Mount Olive, N.J.) in water. The encapsulation efficiency was 55%. In addition, another batch of nanoparticles was prepared which contained a crosslinking agent polydextran aldehyde coupled via a Schiff-base. No conversion of this Schiff-base bond to a covalent one was done by means of a reduction step because such bond is too strong. The Schiff-base crosslinking reaction provided better controlled slow-release regime. The release occurs via a dissociation of the Schiff-base complex due to environmental conditions, such as pH or temperature. The product is stable in water, neutral buffers and in 0.9 wt-% saline. Alternatively, the chemistry used for production of nanoparticles can be any of the combination with the adjustment for FGF incorporation and crosslinking.

EXAMPLE 5

Angiogenic Factor Coating of Polymeric Meshes

For coating of meshes or tubing, a similar multicomponent polymeric system as described in Example 1 was used. A sequential coating of anionic and cationic polymers was applied by allowing the substrates to dry in a laminar flow hood between steps. Tetko polyester mesh product (12×12 mm cut) was used [Precision Woven Screening Media for Healthcare and Specialty Applications, Polyester Medifab 7-285/44, Tetko Inc., Lancaster, N.Y., 1997; Chu, C. C. Classification and general characteristics of suture materials. In: *Wound Closure Biomaterials and Devices*, Chu, C. C., von Fraunhofer, J. A., and Greisler, H. P., eds., CRC Press, Boca Raton, pp. 39–63, 1997; Chu, C. C. Chemical structure and manufacturing processes. In: *Wound Closure Biomaterials and Devices*, Chu, C. C., von Fraunhofer. J. A., and Greisler, H. P., eds., CRC Press, Boca Raton, pp.65–106, 1997], having mesh opening suitable for retaining microcapsules with encapsulated islets (capsules about 0.8–0.5 mm in size) and perfusion of nutrients and products in and out. The core polyanionic and shell cationic solutions were prepared as mentioned in Example 1, except that the core solution contained additional bFGF in quantity of 1–100 µg/ml. Usually, 10 meshes were coated with 1 ml of the above anionic solution (twice) so as the amount bFGF was about 0.1–15 µg/mesh of the above size. The mesh was first immersed into the core solution for a few seconds and allowed to dry for 15 minutes. It was then immersed into the shell solution and again allowed to dry for 15 minutes. The procedure was then repeated over again. The last step included the core solution, thus an anionic outside change on the final product (mesh). Silastic (U.S. Pharmacopoeia class VI) tubing (Fisher, Pittsburgh, Pa.) of 2-mm inner diameter was used to accomplish similar coating. It was perforated to form small openings of about 0.3 mm in size and coated using the procedure as described above for the mesh. Any other similar macroporous material, retaining microcapsules, can be used for the same purpose.

EXAMPLE 6

Angiogenic-inducing Polymeric Vehicle

Specific extracellular matrix molecules can also enhance angiogenesis. Extracellular matrix components (ECM), such as hyaluronic acid, fibronectin, heparin (heparin sulfate), laminin and Matrigel can be considered. Heparin is preferred molecule of choice, because of its high affinity to the FGF family of growth factors as well as to the vascular endothelial growth factor family. These molecules can form electrostatic complexes with the growth factors, which then serve as a reservoir for release of an active form of the factor.

Two separate delivery vehicles (compositions) are possible here. First, a given molecule is incorporated into a core polymeric mixture to serve as a structural component of gelled film or microcapsules. Second, a polymeric capsule is coated with a given angiogenic-stimulating molecule. The polymeric film was prepared as described in Example 1, except that the core polymer contained additional quantity of 0.1 wt-% of heparin (Sigma, St. Louis, Mo.). In the second case, another batch of film (prepared without heparin in the core solution) was subsequently coated with 0.1% wt-% heparin solution.

EXAMPLE 7

Slow Release of Substances

Polymeric film was prepared as described in Example 1, except that the core solution contained $^{125}$I-labeled factor bFGF or alternatively, heparin (Sigma). The bFGF labeling was done by means of a labeling kit (Pierce). The film was then cut into four equal pieces of about 12×10 mm. To measure a release rate, four parallel samples of film were placed in 5 ml test buffer (PBS) on a shaker and successive aliquots were taken arid analyzed. The tracer quantity was assayed using a gamma counter. The permeability was assessed via an efflux method [Prokop, et al., *Water soluble polymers for immunoisolation. II. Evaluation of multicomponent microencapsulation systems*. Advances in Polymer Science, 136: 52–73 (1998)].

Results show that the release rate depends on the gel loading (it is higher for a higher loading) and on surface to volume ratio. Thus, the size and shape of films (and capsules) is a contributing factor. The release rates observed were higher (up to 9%/day) for the factor in the absence of heparin. For gels loaded with heparin, the release rates were 3–5 wt-%/day. The ratios tested were 20/1, 10/1, 2/1, 1/1 and 1/2 of weight bFGF/heparin. Since the molecular weights of heparin and growth factor are similar, these ratios approximate the molar ratios. As other angiogenic growth factors are also known to form complexes with other extracellular matrix components, an addition of these factors to the polymeric formulations may be used to slow the release of growth factors. A similar release experiment was carried out with FGF-loaded nanoparticles, prepared as per Example 4. In this case, because of Schiff-base PDA crosslinking of the growth factor, its release rate was reduced to 0.5–1 wt-%/day. Similar release rates were observed for 0.9 wt-% saline.

EXAMPLE 8

Incubation of Isolated Animal Islets in the Presence of Angiogenic Growth Factors Isolated islets were tested in presence of angiogenic growth factors and polymers to ensure physiologic conditions. Such tests were designed to eliminate possible harmful effects of supraoptimal concentrations of vascularization agents. VEGF stimulates both the insulin content/islet DNA ratio and the accumulation of insulin in an insulinoma cell line culture [Oberg, C., Waltenberger, J., Claesson-Welsh, L., Welsh, M. Expression of protein tyrosine kinases in islet cells: Possible role of the Flk-1 receptor for beta-cell maturation from duct cells, Growth Factors 10: 115–126 (1994); Oberg-Welsh, C., Sandler, S., Anderson, A., and Welsh, M. Effects of vascular endothelial growth factor on pancreatic duct cell replication and the insulin production of fetal islet-like cell clusters in vitro, Molec. Cell. Endocrinol. 126: 125–132 (1997)]. The amount of VEGF are appropriately balanced as its excess can cause a hyperpermeability, microtrombi and hemorrhage.

The rat pancreas digestion and islet purification was carried out using a published procedure [Wang, et al., A new generation capsule and encapsulation system for immunoisolation of pancreatic islets, Nature Biotechnol. 15: 358–362 (1997)]. Islet integrity was evaluated by dithizone stain. Insulin release in response to the glucose challenge, as a function of time, was evaluated in a perfusion system [Wang, et al., Encapsulation system for the immunoisolation of living cells. U.S. Pat. No. 5,997,900] and normalized per equivalent islet number. The islet culturing was carried in presence of RPMI/FCS medium (Sigma). Islet morphology (light microscopy via staining and electron microscopy) was evaluated after 5 days of culturing. Insulin islet content per DNA and culture medium insulin content per islet DNA were also determined after the culturing [Oberg-Welsh, C., Sandler, S., Anderson, A., and Welsh, M. Effects of vascular endothelial growth factor on pancreatic duct cell replication and the insulin production of fetal islet-like cell clusters in vitro, Molec. Cell. Endocrinol. 126: 125–132 (1997)]. Specific antibodies were used to detect levels of vascular tissue-related antigens (proteins) [Oberg-Welsh, et al., Effects of vascular endothelial growth factor on pancreatic duct cell replication and the insulin production of fetal islet-like cell clusters in vitro, Molec. Cell. Endocrinol. 126: 125–132 (1997); Rooman, I., Schit, F., and Bouwens, L. Effect of vascular endothelial growth factor on growth and differentiation of pancreatic ductal epithelium, Lab. Investigat. 76: 225–232 (1997); Sephel, et al., Expression of capillary basement membrane components during sequential phases of wound angiogenesis, Matrix Biol. 15: 263–279 (1996)].

In this example, 1–100 $\mu$g/ml medium of bFGF was tested. The islet morphology, their physiologic status and insulin content per DNA revealed that the optimal concentration of bFGF was 2–4 $\mu$g/ml. It should be noted that this "optimal" quantity might be different in presence of polymeric matrix and extracellular matrix molecules. Results are reported in Table 1 and Table 2. Table 1 and electron microscopic data indicate that the concentration of 1–5 $\mu$g/ml of bFGF (in polymeric solution used for coating) does not result in an impaired islet physiology. From Table 1 it can be concluded that islets proliferate in culture and finish about 5 cell cycles before they go to a quiescent state. For islet encapsulation, islet cells which undergo a 5-day expose in culture after their isolation from pancreas, were used in our encapsulation experiments, as well as fresh islets. Similar results were obtained for neonatal pig islets.

TABLE 1

Effect of bFGF on insulin secretion in culture

| | bFGF content in medium ($\mu$g/ml) | | | |
|---|---|---|---|---|
| | None | 1.0 | 4.0 | 40.0 |
| $\mu$ Units of insulin/$\mu$g islet DNA | 3.74 | 4.08 | 8.85 | 23.75 |
| Standard deviation | 1.42 | 1.46 | 3.55 | 7.12 |
| Number of replicas | 10 | 5 | 5 | 5 |

TABLE 2

Effect of bFGF on islet insulin content

| | Day 0 | Day 5 | Day 5 bFGF 4 mcg/ml |
|---|---|---|---|
| Units of insulin content/$\mu$g islet DNA | 940.3 | 10.5 | 12.5 |
| Standard deviation | 92.0 | 3.8 | 4.3 |
| Number of replicas | 5 | 4 | 4 |

EXAMPLE 9

Biocompatibility Test and Induction of Vascularization

Film implants loaded with 0.1–15 $\mu$g/mesh bFGF were prepared as described in Example 2. They were placed subcutaneously and intraperitoneally into Sprague-Dawley rats and evaluated at days 8, 48 and 96. Visual observation (a hemorrhagic appearance), backed by histology (inflammatory reactions, degree of fibrosis and development of granulation tissue with capillaries), were supplemented by a detection of a specific vascularization marker, using an antibody against Factor VIII stain (von Willebrand factor), a specific lectin I/B4 stain or anti-collagen type IV antibody stain (Vector Laboratories, Burlingame, Calif.) [Sephel, G. C., Kennedy, R. and Kudravi, S. Expression of capillary basement membrane components during sequential phases of wound angiogenesis, Matrix Biol. 15: 263–279 (1996)]. The data collected clearly indicate that angiogenesis can be stimulated by means of immobilized angiogenic factor applied in the form of films. The quantities necessary to induce a capillary network were much higher than those detected as physiologic in the islet culture for bFGF (Example 8). The optimal loading was found to be 1–8 $\mu$g/mesh. The bioavailability (degradation) is an important factor. The polymer coating helped to retain biological activity over a long period of time. Still higher bFGF loading (close to 10 $\mu$g/mesh) yielded a substantial hemorrhagic appearance at the application site. The data indicated that the blood capillaries ingrow into the polymeric mesh and where encapsulated islets will eventually reside and maintain the capillary network over long time without its resorption. Other data on aFGF-coated silastic tubes with openings also indicated that blood capillaries can ingrow into the opening of such tubings.

As a control, biocompatibility of the above-prepared implants (but not loaded with bFGF) was determined in the subcutaneous and intraperitoneal sites in rats. Histology and histochemistry of all implants included standard techniques [Sewell, W. R., Wiland, J. and Craver, B. N. New method of comparing sutures of bovine catgut in three species, Surg. Gynecol. Obstet. 100: 483 (1955); Spector, M., and Lalor, P. A. In vivo assessment of tissue compatibility. In: *Biomaterials Science, An Introduction to Materials in Medicine*, Ratner B D, Hoffman A S, Schoen F J, and Lemons J E, eds., Academic Press, pp. 220–228, 1996]. Implants were retrieved and evaluated. Moderate fibrotic growth (porous fibrous granulation tissue with blood capillaries) was noted on the implant periphery as compared to rather impermeable thick fibrotic capsule outside of control implants.

Alternatively, naked (uncoated) polymeric meshes were formulated into a polymeric bag, by folding a mesh and sewing its sides by a nonadsorbable suture. Such bags were implanted into peritoneum of rats and injected prior the implantation with polymeric capsules loaded with a growth factor (as prepared in Example 3). Similarly as above, such implants developed a capillary bed within and outside of the implant. Similarly, polymeric films loaded with an angiogenic factor prepared as per Example 2, were implanted into the peritoneum of animals and a capillary bed was observed around the films after their harvest from the animals in due time.

EXAMPLE 10

Bioartificial Pancreas in a Three-dimensional Vehicle Stimulating Angiogenesis

The islet is a highly vascularized tissue. In the isolation process, islets are devascularized. The decreased oxygen supply results ultimately in the necrosis of the central β cell-rich islet core. Therefore, early re-establishment of a vascular network to the islet may be crucial. An acceleration of this process will enhance islet survival and improve long-term endocrine function. Because the blood vessels' vascularization originates from the adjacent tissues, it is not intended to generate blood vessels within the islets encapsulated in microcapsules, but outside of the microcapsules, which would facilitate better oxygenation and nutrition of the implant in peritoneum. The capillaries generated outside of the carrier will penetrate via the openings of the mesh (or tubing) and ingrow into the vicinity of microcapsules/islets. Mesh, tubular, film or capsule material, loaded with an angiogenic factor, may be applied as a resident or adjoining material for microcapsules bearing islets.

Encapsulation of isolated islets was performed in a manner similar to procedures already described [Wang, et al., Encapsulation system for the immunoisolation of living cells. U.S. Pat. No. 5,997,900]. After encapsulation, insulin secretion by the encapsulated islets was evaluated by means of a perfusion system. Microcapsules were aseptically introduced into a polymeric mesh-bag. Prior that the mesh was sewn into the bag by means of a surgical suture and coated, as described in Example 5. The three-dimensional structure was placed intraperitoneally into diabetic C57/B16 mice (streptozotocin-induced). The fate of the transplant was followed over a six-month period. As a routine check, blood sugar levels were monitored weekly (One-touch glucometer). Routine histology, histochemistry and immunochemistry of vascularization were performed on animals sacrificed at 1, 6, 12 and 24 weeks.

The quality and quantity of the vascularized structure, supported by a positive detection of collagen type IV of the basement membrane of endothelial cell lining (as in Example 9) and by a detection of endothelial cell's factor VIII molecule was evident. A limited number of experiments were performed with recovered islets (at the end of 6 months). They were washed and perfused and assessed for insulin release capability. The release was about 80% of the freshly isolated islet response. Control experiment (without bFGF coating) showed only 50% response. In another experiment, a coated meshed bag was implanted and allowed to vascularize for 2 weeks prior the injection of encapsulated islets. Results were similar to those above. In still another experiment, islets were encapsulated together with a growth factor as described in Example 3. In this case a control experiment contained no bFGF in capsules. Alternatively, microencapsulated islets were placed into peritoneum (or kidney capsule) together with a polymeric film loaded with an angiogenic factor, as described in Example 2 (a control experiment contained a non-loaded film). One more test contained encapsulated islets and angiogenic growth factor-loaded nanoparticles, prepared per Example 4, both injected into peritoneum of animals. In all these tests, the benefit of providing angiogenic factor for encapsulated islets by means of suitable delivery vehicle prior or after their implantation was clearly demonstrated.

EXAMPLE 11

Acceleration of Wound Healing by a Growth Factor

Film implants loaded with 10 μg/ml of film volume PDGF (platelet derived growth factor) were prepared as described in Example 2. They were cut into 8-mm discs (50 mm$^2$), containing 3.4 μg PDGF/disc, and their efficiency was tested in rat incisions. Sprague-Dawley rats were incised externally. The delivery vehicle was placed at the base of the wound and then closed over with Michel wound clips. Each rat contained 3 test sites and 1 control site. The animals were sacrificed and wound sites were harvested for histological and biomechanical analysis at 7, 14 and 21 days after surgery to determine tensile properties and tissue response. The collected data clearly indicated that the wound healing was accelerated in the presence of PDGF by 50% as compared to control.

EXAMPLE 12

Removal of Undesirable Growth Factors by Nonloaded Vehicles

Polymeric films were prepared as described in Example 1. They were cut into four pieces and each was equilibrated for one hour in 3 ml of solution containing 10 μm $^{125}$I-bFGF. Gelled films were then removed from solution, quickly washed with distilled water and the radioactivity of the gel was measured. The percentage of the original activity uptake amounted to 85%. A similar experiment was done with films containing heparin and other ECM molecules. Such implants may have an application in treating rheumatic disease.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A polymeric drug delivery vehicle comprised of a polyanionic/polycationic polymer, said polyanionic/polycationic polymer comprising:
   a) at least two or more polyanions selected from the group consisting of kappa carrageenan, low-esterified pectin, polyglutamic acid, carboxymethylcellulose, chondroitin sulfate-6, chondroitin sulfate-4, collagen, high viscosity sodium alginate, and cellulose sulfate;
   b) one or more polycation(s) selected from the group consisting of polyvinylamine, spermine hydrochloride, protamine sulfate, polyethyleimine, polyethyleimine-exthoxylated, polyethyleimine-epichlorhydrin modified, quartenized polyamide, polydiallyldimethyl ammonium chloride-co-acrylamide, low molecular-weight chitosan, poly(methylene-co-guanidine) and calcium chloride;
   c) one or more small cation(s) selected from the group consisting of sodium, potassium, or calcium; and,
   d) one or more protein(s) selected from the group consisting of angiogenic stimulating factors, growth factors, and extracellular matrix proteins; wherein said protein(s) is incorporated into said polymer.

2. The polymeric drug delivery vehicle of claim 1, wherein said polyanions comprise a combination of high viscosity sodium alginate and cellulose sulfate.

3. The polymeric drug delivery vehicle of claim 1, wherein said polycations comprise a combination of poly(methylene-co-guanidine)hydrochloride and calcium chloride.

4. The polymeric drug delivery vehicle of claim 1, wherein said protein is an angiogenic stimulating factor selected from the group consisting of vascular endothelial growth factor, angiopoietin, fibroblast growth factors, and transforming growth factor β.

5. The polymeric drug delivery vehicle of claim 1, wherein said protein is platelet derived growth factor.

6. The polymeric drug delivery vehicle of claim 1, wherein said protein is an extracellular matrix protein selected from the group consisting of heparin, heparan sulfate, hyaluronic acid, fibronectin, perlecan and laminin.

7. A method of stimulating vascularization around cells transplanted into an individual, comprising the steps of:
   a) encapsulating said cells in the polymeric drug delivery vehicle of claim 4; and,
   b) implanting the encapsulated cells into said individual.

8. The method of claim 7 comprising the further step of:
   a) prevascularizing an implantation site in said individual for at least 2 weeks prior to implanting the encapsulated cells with a retrievable composition comprised of a polyanionic/polycationic polymer comprised of: two or more polyanions; one or more polycation(s); one or more small cation(s) selected from the group consisting of sodium, potassium, or calcium; and, an angiogenic stimulating factor selected from the group consisting of vascular endothelial growth factor, angiopoietin, fibroblast growth factors, and transforming growth factor β.

9. The method of claim 8, wherein said retrievable composition is selected from the group consisting of a mesh and a capsule.

10. The method of claim 7, wherein said cells are pancreatic islet cells.

11. The method of claim 10, wherein a growth factor is implanted along with encapsulated pancreatic islet cells.

12. The method of claim 11, wherein said growth factor is incorporated into a polymeric drug delivery vehicle selected from the group consisting of a polymeric film, microcapsules, and nanoparticles.

13. The method of claim 12, wherein said growth factor is crosslinked via Schiff-base polydextran aldehyde complex to the polyanionic/polycationic polymer of the polymeric drug delivery vehicle.

14. The method of claim 12, wherein microencapsulated pancreatic islet cells and nanoparticulate FGF are implanted in a capsule in the peritoneum of the kidney.

15. A method of accelerating wound healing in an individual in need of such treatment, comprising the step of placing the polymeric-drug delivery vehicle of claim 1 incorporating a growth factor in proximity to a wound.

16. The method of claim 15, wherein said growth factor is platelet derived growth factor.

17. The method of claim 15, wherein said polymeric-drug delivery vehicle is selected from the group consisting of a film containing fibroblast growth factor(s), nanoparticle of fibroblast growth factor(s), and fibroblast growth factor hydrogel-coated, bioresorbable film for wound healing.

18. The method of claim 17, wherein said fibroblast growth factor(s) is crosslinked to said polymeric drug delivery vehicle via polydextran aldehyde.

19. A method of forming a polymeric drug delivery vehicle comprised of a polyanionic/polycationic polymer wherein said polycation contacts said polyanion through a dialysis process, comprising the steps of:
   a) introducing a polyanion solution into a dialysis cassette; wherein the polyanion solution comprises a polyanion selected from the group consisting of kappa carrageenan, low-esterified pectin, polyglutamic acid, carboxymethylcellulose, chondroitin sulfate-6, chondroitin sulfate-4, collagen, high viscosity sodium alginate, and cellulose sulfate and mixtures thereof;
   b) immersing said cassette in a stirred reactor containing a polycation solution; wherein the polycation solution comprises a polycation selected from the group consisting of polyvinylamine, spermine hydrochloride, protamine sulfate, polyethyleimine, polyethyleimine-exthoxylated, polyethyleimine-epichlorhydrin modified, quartenized polyamide, polydiallyldimethyl ammonium chloride-co-acrylamide, low molecular-weight chitosan, poly(methylene-co-guanidine) and calcium chloride and mixtures thereof and,
   c) allowing dialysis to proceed for a period of time to allow formation of a polyanionic/polycationic polymer shell comprising said drug delivery vehicle; wherein a protein is incorporated into the polymer drug delivery vehicle by adding said protein to said polyanion solution.

20. The method of claim 19, wherein said polyanion solution comprises high viscosity sodium alginate and cellulose sulfate.

21. The method of claim 20, wherein the concentration of said polyanion in said solution is 0.6% w/v.

22. The method of claim 19, wherein said polycation solution comprises poly(methylene-co-guanidine) hydrochloride and calcium chloride.

23. The method of claim 22, wherein the concentration of said polycation in said solution is 1.0% w/v.

24. The method of claim 22, wherein said protein is selected from the group consisting of angiogenic stimulating factors, growth factors, and extracellular matrix proteins.

25. The method of claim 24, wherein said growth factor is basic fibroblast growth factor.

26. The method of claim 25, wherein said basic fibroblast growth factor is present at a concentration ranging from 0.1–15 µg/ml.

27. The method of claim 22, wherein said growth factor is platelet derived growth factor.

28. The method of claim 27, wherein said platelet derived growth factor is present at a concentration of 1–20 µg/ml.

29. The method of claim 19, comprising the further step of neutralizing the positive charge present on the surface of the polyanionic/polycationic polymer comprising said polymeric drug delivery vehicle by coating said polymeric drug delivery vehicle with a dilute anionic polymer solution selected from the group consisting of alginate and carboxymethylcellulose.

30. The method of claim 29, wherein said dilute anionic polymer solution is at a concentration of 0.1% w/v.

31. A method of coating prefabricated materials with a polyanionic/polycationic polymer containing an angiogenic stimulating factor, comprising the steps of:
   a) applying a coat of a polyanion solution to said material, wherein said solution contains an angiogenic stimulating factor; wherein said angiogenic stimulating factor is incorporated into said polymer
   b) allowing said polyanion coat to dry;
   c) applying a coat of a polycation solution to said material;
   d) allowing said polycation coat to dry; and,
   e) sequentially repeating steps a through d.

32. An assembly for the implantation of non-human animal cells in an individual, comprising microcapsules of said cells attached to a support material, wherein said assembly has been coated with an angiogenic stimulating factor by the method of claim 31.

33. The assembly of claim 32, wherein said support material is selected from the group consisting of retrievable polymeric mesh and perforated tubing.

34. The assembly of claim 32, wherein said cells are pancreatic islet cells.

* * * * *

UNITED STATES PATENT AND TRADEMARK OFFICE
CERTIFICATE OF CORRECTION

PATENT NO. : 6,383,478 B1
DATED : May 7, 2002
INVENTOR(S) : Ales Prokop, Mikhail Dikov, Phillip Williams and Jeffrey Davidson It is certified that error appears in the above-identified patent and that said Letters Patent is hereby corrected as shown below:

Column 1,
Line 12, should read -- through grant number AR41943 from the National Institutes of Health. --

Signed and Sealed this

Twenty-third Day of July, 2002

Attest:

Attesting Officer

JAMES E. ROGAN
Director of the United States Patent and Trademark Office